United States Patent
Erickson et al.

(10) Patent No.: US 7,223,248 B2
(45) Date of Patent: May 29, 2007

(54) PACKAGED MEDICAL DEVICE WITH A DEPLOYABLE DERMAL TISSUE PENETRATION MEMBER

(75) Inventors: Brian Erickson, Woodbury, MN (US); John Allen, Mendota Heights, MN (US)

(73) Assignee: LifeScan, Inc., Milpitas, CA (US)

( * ) Notice: Subject to any disclaimer, the term of this patent is extended or adjusted under 35 U.S.C. 154(b) by 435 days.

(21) Appl. No.: 10/640,296

(22) Filed: Aug. 13, 2003

(65) Prior Publication Data

US 2005/0036909 A1 Feb. 17, 2005

(51) Int. Cl.
A61B 5/00 (2006.01)

(52) U.S. Cl. ............ 600/584; 600/583; 600/573; 606/181

(58) Field of Classification Search ........ 600/573, 600/576, 583, 584; 606/181, 182
See application file for complete search history.

(56) References Cited

U.S. PATENT DOCUMENTS

| | | | |
|---|---|---|---|
| 5,201,324 A * | 4/1993 | Swierczek | 600/583 |
| 5,231,993 A * | 8/1993 | Haber et al. | 600/583 |
| 5,279,294 A * | 1/1994 | Anderson et al. | 600/322 |
| 5,324,302 A | 6/1994 | Crouse | |
| 5,407,070 A | 4/1995 | Bascos et al. | |

(Continued)

FOREIGN PATENT DOCUMENTS

| | | |
|---|---|---|
| EP | 1360935 A | 12/2003 |
| WO | WO 01/64105 A1 | 9/2001 |
| WO | WO 02/49507 A1 | 6/2002 |
| WO | WO 03/015627 A2 | 2/2003 |

OTHER PUBLICATIONS

European Search Report issued by European Patent Office, Berlin, Germany, for Application 04254887.5; dated Nov. 17. 2004.
Allen, John J. et al., "Integrated Lance and Strip for Analyte Measurement", U.S. Appl. No. 10/460,030, filed Jun. 11, 2003.
Allen, John J. et al., "Method of Analyte Measurement Using Integrated Lance and Strip", U.S. Appl. No. 10/460,106, filed Jun. 11, 2003.

*Primary Examiner*—Max F. Hindenburg
*Assistant Examiner*—H. Q. Nguyen (57) ABSTRACT

A packaged medical device includes upper and lower flexible sheets, a lance body and a test strip. The lance body includes upper and lower surfaces, an opening that extends between the upper and lower surfaces and a dermal tissue penetration member that projects into the lance body opening. The test strip has an opening therethrough and is attached to the lance body lower surface such that the dermal tissue penetration member is operatively aligned with the test strip opening. The upper flexible sheet is attached to the lance body upper surface and covers the lance body opening, while the lower flexible sheet is detachably attached to the test strip and covers the test strip opening. The upper flexible sheet, lance body and test strip are configured such that, when the lower flexible sheet has been detached to uncover the test strip opening, the upper flexible sheet, lance body and test strip can be bent to deploy the dermal tissue penetration member from the lance body opening. A kit includes the packaged medical device described above and a deployment device for detaching the lower flexible sheet and bending the upper flexible sheet, lance body and test strip to deploy the dermal tissue penetration member. A method for deploying a dermal tissue penetration member of a packed medical device includes providing the packaged medical device described above, detaching the lower flexible sheet to uncover the test strip opening and bending the upper flexible sheet, lance body and test strip to deploy the dermal tissue penetration member.

13 Claims, 4 Drawing Sheets

U.S. PATENT DOCUMENTS

| | | |
|---|---|---|
| 6,140,549 A | 10/2000 | Pompei, Jr. |
| 6,488,828 B1 | 12/2002 | Bhullar et al. |
| 2002/0099308 A1* | 7/2002 | Bojan et al. ............... 600/573 |
| 2002/0168290 A1 | 11/2002 | Yuzhakov et al. |
| 2003/0013992 A1* | 1/2003 | Uchigaki et al. ........... 600/584 |
| 2003/0069509 A1* | 4/2003 | Matzinger et al. .......... 600/504 |
| 2003/0083686 A1 | 5/2003 | Freeman et al. |
| 2003/0143113 A2 | 7/2003 | Yuzhakov et al. |
| 2004/0049129 A1* | 3/2004 | Qi ............................... 600/576 |
| 2004/0127929 A1* | 7/2004 | Roe ............................ 606/181 |
| 2005/0049522 A1 | 3/2005 | Allen |
| 2006/0030789 A1* | 2/2006 | Allen ......................... 600/583 |
| 2006/0100543 A1* | 5/2006 | Raney et al. ................ 600/583 |

\* cited by examiner

PACKAGED MEDICAL DEVICE WITH A DEPLOYABLE DERMAL TISSUE PENETRATION MEMBER

BACKGROUND OF THE INVENTION

1. Field of the Invention

The present invention relates, in general, to medical devices and associated packages and, in particular, to packaged medical devices with a deployable dermal tissue penetration member.

2. Description of the Related Art

A variety of medical devices require packaging to, for example, protect the medical device from damage prior to use and to maintain sterility of the medical device. For medical devices that combine a dermal tissue penetration member (e.g., a lancet or micro-needle) with a test strip, the associated package should provide for deployment of the dermal tissue penetration member during use, while also providing for protection of a user from inadvertent contact with the dermal tissue penetration member prior and subsequent to use. Furthermore, the packaging should provide humidity resistance for the test strip during storage.

A single-use medical device calls for a medical device package that is inexpensive, disposable, and has a slim profile. Although it is conceivable that rigid injection molded medical device packages could be designed to provide protection of medical devices enclosed therein, it is likely that their cost and potentially cumbersome manual deployment (i.e., opening) procedures would be less than ideal.

Still needed in the field, therefore, is a packaged medical device with a deployable dermal tissue penetration member that does not require cumbersome manual opening procedures, yet still provides for sterile protection of a medical device enclosed therein. Furthermore, the packaged medical device should provide protection for the dermal tissue penetration member from damage, humidity or contamination during storage, as well as protection for a user from accidental contact with the dermal tissue penetration member prior and subsequent to use. In addition, it would be desirable for the packaged medical device to have a slim profile and be inexpensive.

SUMMARY OF THE INVENTION

Packaged medical devices with dermal tissue penetration members according to embodiments of the present invention do not require cumbersome manual opening procedures for deployment of the dermal tissue penetration member, yet still provide for protection of a medical device enclosed therein for sterility, as well as from damage, humidity and/or contamination during storage. Furthermore, the packaged medical devices protect a user from accidental contact with the dermal tissue penetration member prior and subsequent to use. In addition, the packaged medical devices can be manufactured using inexpensive lamination techniques that result in a packaged medical device with a slim profile. Furthermore, methods and kits for deploying the dermal tissue penetration member of packaged medical devices according to exemplary embodiments of the present invention are simple to employ.

A packaged medical device according to an exemplary embodiment of the present invention includes upper and lower flexible sheets, a lance body and a test strip. The lance body includes lance body upper and lower surfaces, a lance body opening that extends from the lance body upper surface to the lance body lower surface, and a dermal tissue penetration member that projects into the lance body opening.

The test strip of the packaged medical device has a test strip opening therethrough that is in a general alignment with the lance body opening. The test strip of the packaged medical device is attached to the lance body lower surface such that the dermal tissue penetration member is operatively aligned with the test strip opening.

The upper flexible sheet of the packaged medical device is attached to the lance body upper surface and covers the lance body opening. The lower flexible sheet of the packaged medical device is detachably attached to the test strip and covers the test strip opening.

Furthermore, the upper flexible sheet, lance body and test strip are configured such that, when the lower flexible sheet has been at least partially detached from the test strip to uncover the test strip opening, the upper flexible sheet, lance body and test strip can be bent to deploy the dermal tissue penetration member from the lance body opening.

A kit according to an exemplary embodiment of the present invention includes the packaged medical device described above and a deployment device. The deployment device detaches the lower flexible sheet from the test strip to uncover the test strip opening and bends the upper flexible sheet, lance body and test strip to deploy the dermal tissue penetration member from the lance body opening.

A method for deploying a dermal tissue penetration member of a packaged medical device according to an exemplary embodiment of the present invention includes providing the packaged medical device described above, detaching the lower flexible sheet from the test strip to uncover the test strip opening and bending the upper flexible sheet, lance body and test strip to deploy the dermal tissue penetration member from the lance body opening.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings, of which.

DETAILED DESCRIPTION OF THE INVENTION

Figure 1:
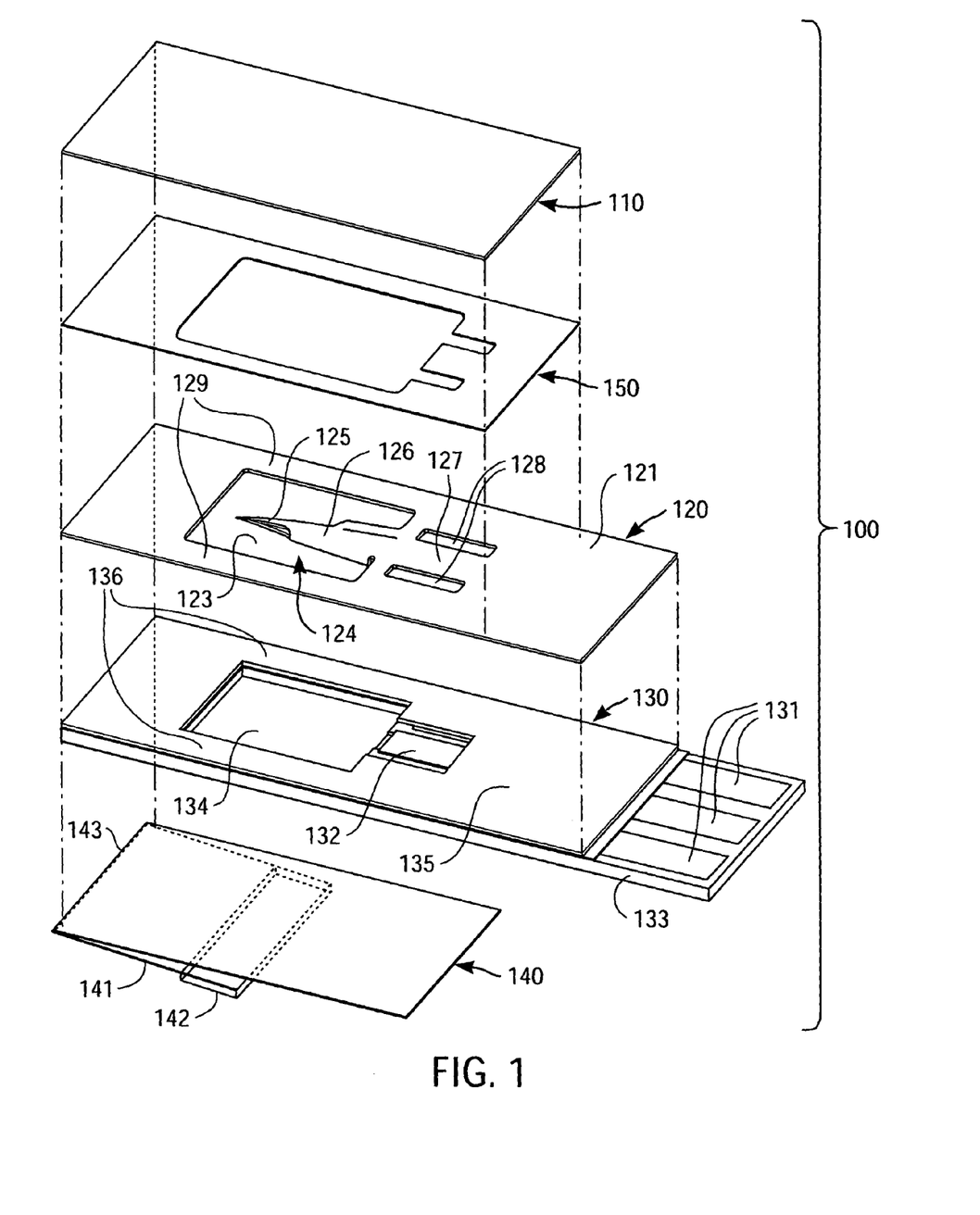
FIG. 1 is an exploded perspective view of an exemplary embodiment of a packaged medical device according to the present invention.

FIG. 1 is a simplified exploded perspective view of a packaged medical device 100 according to an exemplary embodiment of the present invention, with the broken vertical lines of FIG. 1 indicating alignment of various components of packaged medical device 100 and the dashed lines indicating certain features that are hidden from view due to the perspective nature of FIG. 1. Packaged medical device 100 includes an upper flexible sheet 110, a lance body 120, a test strip 130, and a detachable lower flexible sheet 140.

One skilled in the art will appreciate that the lance body 120 and test strip 130, in combination, constitute a medical device and, in particular, an integrated medical device. Further details regarding the type of integrated medical device depicted in FIG. 1 can be found in co-pending U.S. patent application Ser. No. 10/460,106 (filed Jun. 11, 2003, entitled "Method of Analyte Measurement Using Integrated Lance and Strip") and Ser. No. 10/460,030 (filed Jun. 11, 2003, entitled "Integrated Lance and Strip for Analyte Measurement"), which are fully incorporated herein by reference. Moreover, once apprised of the present disclosure, one skilled in the art will recognize that a variety of other medical devices can be beneficially configured as packaged medical devices according to the present invention.

Those skilled in the art will also recognize that packaged medical devices according to the present invention can be placed in a secondary package, for example, in a vial or a cartridge configured for dispensing such packaged medical devices. The secondary package can be constructed of material containing desiccant or can contain separately packaged desiccant for keeping contents of the secondary package moisture free.

Lance body 120 includes a lance body upper surface 121, a lance body lower surface (not visible in FIG. 1), and a lance body opening 123 that extends from lance body upper surface 121 to lance body lower surface. Lance body 120 also includes a dermal tissue penetration member 124 that projects into lance body opening 123. Lance body 120 of FIG. 1 is commonly referred to in the field as a monolithic lance and can be fabricated, using, for example, progressive die stamping techniques.

Dermal tissue penetration member 124 of lance body 120 includes a needle tip 125, and a channel 126. Dermal tissue penetration member 124 is a lancet configured to pierce a user's skin (i.e., dermal tissue), draw a sample (e.g., a whole blood sample) from the user and deliver the sample to reaction area 132 (described below) of test strip 130. Dermal tissue penetration member 124 can be fabricated by, for example, progressive die stamping, as disclosed in International Application No. PCT/GB01/05634 (published as WO 02/49507 on Jun. 27, 2002) and U.S. patent application Ser. No. 10/143,399, both of which are fully incorporated herein by reference.

Lance body 120 further includes a cell-defining portion 127, and two vents 128. In addition, lance body opening 123 is bounded on three sides by a lance body perimeter 129, which mirrors an outline of three sides of test strip opening 134 (described below) of test strip 130.

In the embodiment of FIG. 1, upper flexible sheet 110 is attached to a portion of the lance body upper surface 121 by an adhesive layer 150 such that upper flexible sheet 110 covers lance body opening 123. It should be noted, however, that upper flexible sheet 110 of packaged medical device 100 is not attached to dermal tissue penetration member 124.

Adhesive layer 150 can be any suitable adhesive layer known to one skilled in the art including, but not limited to, pressure-sensitive adhesive layers. Such pressure-sensitive adhesive layers can be manufactured by conventional techniques including, for example, screen printing, gravure coating and slot coating. Alternatively, a suitable adhesive layer can be pre-formed by die cutting, laser scribing or punching an adhesive material before lamination onto an underside of upper flexible sheet 110. Furthermore, the adhesive layer can be formed of a double-sided pressure-sensitive adhesive, a UV-cured adhesive, a heat-activated adhesive or a thermosetting plastic. As a non-limiting example, the adhesive may be formed by screen printing a pressure-sensitive adhesive such as, for example, a water-based acrylic copolymer pressure-sensitive adhesive (e.g., part #A6435, commercially available from Tape Specialties LTD in Tring, Herts, United Kingdom).

Upper flexible sheet 110 can be formed of any suitable material, such as surgical craft paper, Tyvek or other material which is impervious to air and/or air-borne bacteria in order to provide packaged medical device 100 with a sterile protective barrier. In addition, upper flexible sheet 110 can be puncture resistant to reduce the possibility of inadvertent penetration by dermal tissue penetration member 124. Furthermore, upper flexible sheet 110 can be configured to provide humidity protection for test strip 130, by forming upper flexible sheet 110 of a heavy polymer film, metal foil, or a composite of a metal foil and thin polymer film.

Test strip 130 includes electrode contacts 131, a reaction area 132, an insulated substrate 133, a test strip opening 134, an adhesive coating 135 and a three-sided test strip perimeter 136. As depicted in FIG. 1, test strip 130 is an electrochemical glucose measurement test strip fabricated using conventional screen printing techniques. However, one skilled in the art will realize that test strips for use in packaged medical devices according to the present invention can have, but are not limited to, any suitable electrochemical and photometric configuration and that for illustrative purposes only, test strip 130 of FIG. 1 is illustrated as an electrochemical glucose measurement test strip. Moreover, those skilled in the art will appreciate that suitable test strips for use in packaged medical devices according to the present invention are not limited to test strips for the measurement of glucose but can also be test strips used to measure, for example, ketones, glycated proteins (such as glycated albumin), coagulation parameters and/or cholesterol of a sample.

Test strip 130 is attached to the lance body lower surface such that dermal tissue penetration member 124 is operatively aligned with the test strip opening 134. In the embodiment of FIG. 1, lance body 120 is laminated to test strip 130 such that the cell-defining portion 127 of lance body 120 lies directly above reaction area 132, thereby serving to define a reaction cell. Vents 128 of lance body 120 serve to define side edges of the reaction cell and to minimize the total sample volume of the reaction cell. By minimizing the total sample volume, the functionality of test strip 130 is optimized. Further details regarding the exemplary reaction cell and vents construction can be found in co-pending U.S. patent application Ser. No. 60/458,242 (filed Mar. 28, 2003, entitled "Integrated Lance and Strip for Analyte Measurement"), Ser. No. 60/459,465 (filed Mar. 28, 2003, entitled "Method of Analyte Measurement using Integrated Lance and Strip") Ser. No. and 60/422,228 (filed Oct. 30, 2002, entitled "Improved Method of Lancing Skin for the Extraction of Blood"), which are fully incorporated herein by reference.

In the embodiment of FIG. 1, electrode contacts 131 of test strip 130 extend beyond lance body 120 and upper flexible sheet 110. This extension of the electrode contacts simplifies the establishment of an electrical connection between the electrode contacts and external device(s) (e.g., a meter). Those skilled in the art will recognize that although three electrode contacts 131 are shown in FIG. 1 for the purpose of illustration, test strips for use in packaged medical devices according to the present invention can include those with no electrode contacts and, in general, those with at least one electrode contact.

Test strip 130 can be fabricated using conventional screen-printing techniques and can be printed on, for example, an insulated substrate (such as insulated substrate 133). Reaction area 132 can, for example, include reagents, insulation layers, and carbon electrodes that are in electrochemical communication with electrode contacts 131.

Test strip opening 134 is adjacent to reaction area 132 and provides clearance for channel 126 of dermal tissue penetration member 124. Adhesive coating 135 can be formed, for example, of a pressure-sensitive adhesive that is printed on insulated substrate 133 by methods known to those skilled in the art. In addition, adhesive coating 135 and insulated substrate 133 can be selected and configured to provide a packaged medical device with sterility and/or humidity protection.

Lower flexible sheet 140 is detachably attached (e.g., sealed) to a lower surface of insulated substrate 133 and covers test strip opening 134. Lower flexible sheet 140 can be laminated to insulated substrate 133 in a detachable manner that provides for easy removal of lower flexible sheet 140 from test strip 130 by, for example, peeling of the lower flexible sheet 140 away from test strip 130. Any suitable adhesive known to one skilled in the art can be employed for this purpose including, but not limited to, cold-seal adhesives, heat-seal adhesives and releasable adhesives available from, for example, 3M, Basic Adhesives and Avery Dennison.

Lower flexible sheet 140 incorporates a flap 141, which is folded back upon lower flexible sheet 140, and a tab 142 of sufficient thickness to enable a person or device to grip and pull tab 142 away from a folded edge 143 of lower flexible sheet 140. Examples of suitable materials for lower flexible sheet 140 are the same as those described above for upper flexible sheet 110. In addition, tab 142 can be formed, for example, by processes known to those skilled in the art, including successively rolling material into a flattened coil or laminating a separate strip of material (such as a plastic sheet or paper card stock).

The upper flexible sheet 110, lance body 120, and test strip 130 of packaged medical device 100 are configured such that, when the lower flexible sheet 140 has been detached from test strip 130 such the test strip opening 134 is uncovered, the upper flexible sheet 110, lance body 120 and test strip 130 can be bent to deploy the dermal tissue penetration member 124 from the lance body opening 123. In the embodiment of FIGS. 1 (and as illustrated in FIGS. 5A–5D) dermal tissue penetration member 124 passes through test strip opening 134 as it is deployed from lance body opening 123. This deployment of the dermal tissue penetration member is further described and illustrated with regard to FIGS. 5A–5D below.

Since packaged medical device 100 can be formed entirely of laminated structures, it is inexpensive and of a slim profile. In addition, enclosure by upper and lower flexible sheets 110 and 140 serves to provide damage, contamination and humidity protections, while three-sided lance body perimeters 129 of lance body 120 and three-sided test strip perimeters 136 of test strip 130 provide damage protection for the dermal tissue penetration member prior to its deployment. Furthermore, the operative alignment of the test strip and lance body openings and the detachable nature of the lower flexible sheet enable ready manual and/or mechanical deployment of the dermal tissue penetration member from within the lance body opening.

Figure 2:
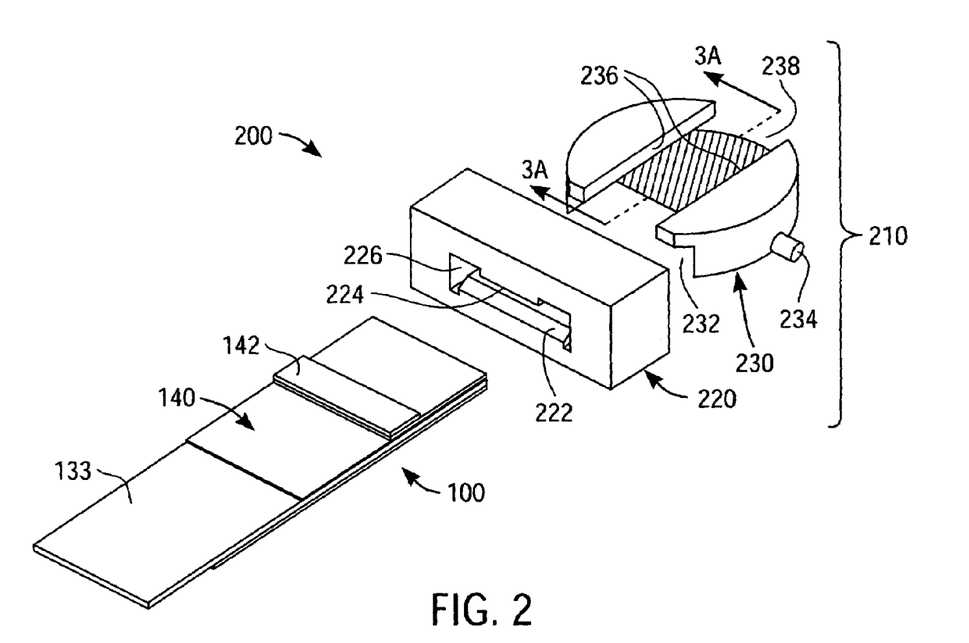
FIG. 2 is a perspective view of an exemplary embodiment of a kit according to the present invention that includes the packaged medical device of FIG. 1 and a deployment device.

FIG. 2 is a perspective view of a kit 200 that includes packaged medical device 100 of FIG. 1 and a deployment device 210. Deployment device 210 is configured to (i) detach lower flexible sheet 140 from test strip 130, thereby uncovering test strip opening 134; and (ii) bend upper flexible sheet 110, lance body 120 and test strip 130 to deploy dermal tissue penetration member 124 from lance body opening 123. If desired, deployment deice 210 can also include at least one electrical connector (not shown) for establishing an electrical connection between an external device (such as a meter, also not shown) and electrode contact(s) of packaged medical device 100. Any suitable electrical connector known those of skill in the art can be employed.

In the embodiment of FIG. 2, deployment device 210 includes a stripping block 220, which detaches lower flexible sheet 140 from test strip 130 of packaged medical device 100. If desired, stripping block 220 can include the aforementioned electrical connector.

Deployment device 210 also includes a folding block 230, which bends upper flexible sheet 110, lance body 120 and test strip 130 to cause the dermal tissue penetration member 124 to deploy from the lance body opening 123. The bending serves to deploy the dermal tissue penetration member from within the lance body opening by essentially moving three-sided lance body perimeter 129, three-sided test strip perimeter 136 and upper flexible sheet 110 away from the dermal tissue penetration member.

The folding can, for example, place these three-sided lance body and test strip perimeters and the bent portion of the upper flexible sheet into an essentially perpendicular orientation with respect to the remainder of the test strip and lance body such that the dermal tissue penetration member 124 is exposed and readied to puncture a user's dermal tissue. A perpendicular orientation has the benefit of placing the three-sided lance body perimeter, three-sided test strip perimeter and upper flexible sheet in positions where they do not interfere with use of the deployed dermal tissue penetration member to lance a user's skin.

Stripping block 220 includes a lead-in chamber 222, a stripping edge 224 and a stripping block opening 226. Stripping block opening 226 is configured such that, with the exception of tab 142, packaged medical device 100 can easily pass through it. The configuration is such that tab 142 is prevented from passing beyond stripping edge 224 of stripping block 220. Stripping block 220, therefore, serves to at least partially detach (e.g., "peel") lower flexible sheet 140 from test strip 130, thereby uncovering test strip opening 134, as packaged medical device 100 is moved through stripping block opening 226.

Folding block 230 of deployment device 210 is positioned distally from stripping block 220. Folding block 230 includes a first folding block opening 232, an axis pin 234, lips 236 and a second folding block opening 238. First folding block opening 232 is of a dimension sufficient to accept packaged medical device 100 as packaged medical device 100 emerges from stripping block 220 (for example, first folding block opening 232 can have a width of approximately 6 mm and a height of approximately 0.8 mm). Folding block 230 can, if desired, be provided with a stop member (not shown) that defines complete insertion of a packaged medical device into folding block 230 by physically preventing over insertion of the packaged medical device.

Axis pin 234 is configured to provide for folding block 230 to pivot through an arc in the range of, for example, approximately 90 degrees to 100 degrees. An arc of 90 degrees will produce the perpendicular orientation discussed above. Although an arc of greater than 100 degrees could be employed, as the arc angle is increased there is also an increased risk of deleterious shearing between, and separation of, the lance body and test strip.

When medical device package 100 is inserted into folding block 230, folding block 230 is mechanically turned to deploy dermal tissue penetration member 124 from lance body opening 123. In this regard, folding block 230 has two lips 236 that define the second folding block opening 238 (for example, a second folding block opening with a width of 5.5 mm wide and a height of 0.7 mm). Second folding block opening 238 is constructed to have a width that is greater than the width of dermal tissue penetration member 124, and preferably as wide as lance body opening 123, such that when folding block 230 bends test strip 130, lance body 120 and upper flexible sheet 110, dermal tissue penetration member 124 is able to pass through second folding block opening 238.

Stripping and folding blocks of the present invention can be formed of any suitable material and can be manufactured using any suitable technique known to one skilled in the art. For example, the stripping and folding blocks can be formed of polycarbonate, acetal, stainless steel or aluminum and can be manufactured using injection molding, die casting or machining techniques.

Figure 3:
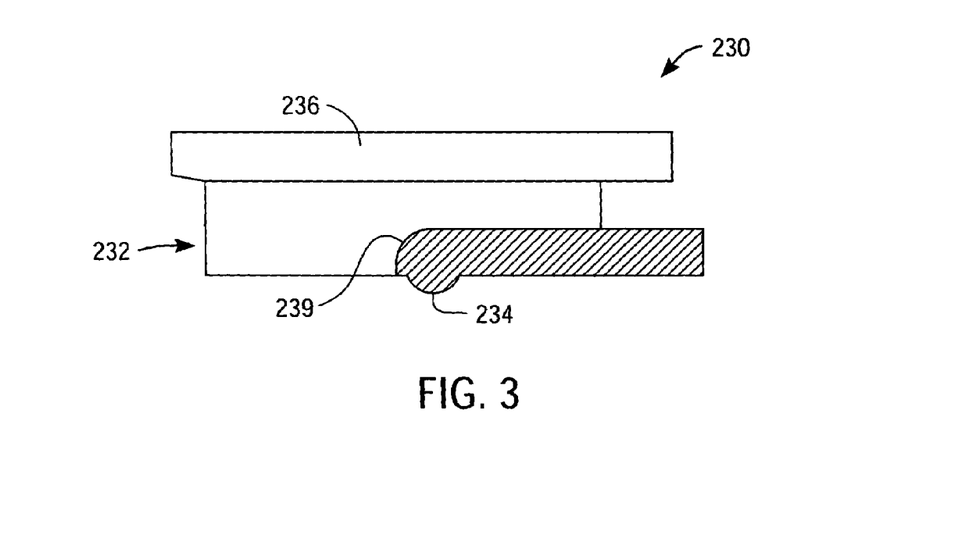
FIG. 3 is a schematic, cross-sectional view of the deployment device of FIG. 2 taken along line 3A—3A of FIG. 2.

FIG. 3 is a cross-sectional view of folding block 230 of deployment device 210 taken along line 3A—3A in FIG. 2. FIG. 3 depicts the manner in which folding block 230 includes a rounded folding edge 239 that is located distal to, and concentric with, axis pin 234. Rounded folding edge 239 is configured to facilitate the bending of test strip 130 and lance body 120 as described above with respect to FIG. 1. In particular, the rounded nature of rounded folding edge 239 provides for a controlled bending since the natural form of a bend is rounded, as well as for increased control of a packaged medical device subsequent to folding Further, a rounded folding edge facilitates the entry of the packaged medical device into the folding block.

FIGS. 4 and 5A through 5D serve to illustrate a sequence of steps in a process 400 for deploying dermal tissue penetration member 124 of packaged medical device 100, according to an exemplary embodiment of the present invention.

Figure 4:
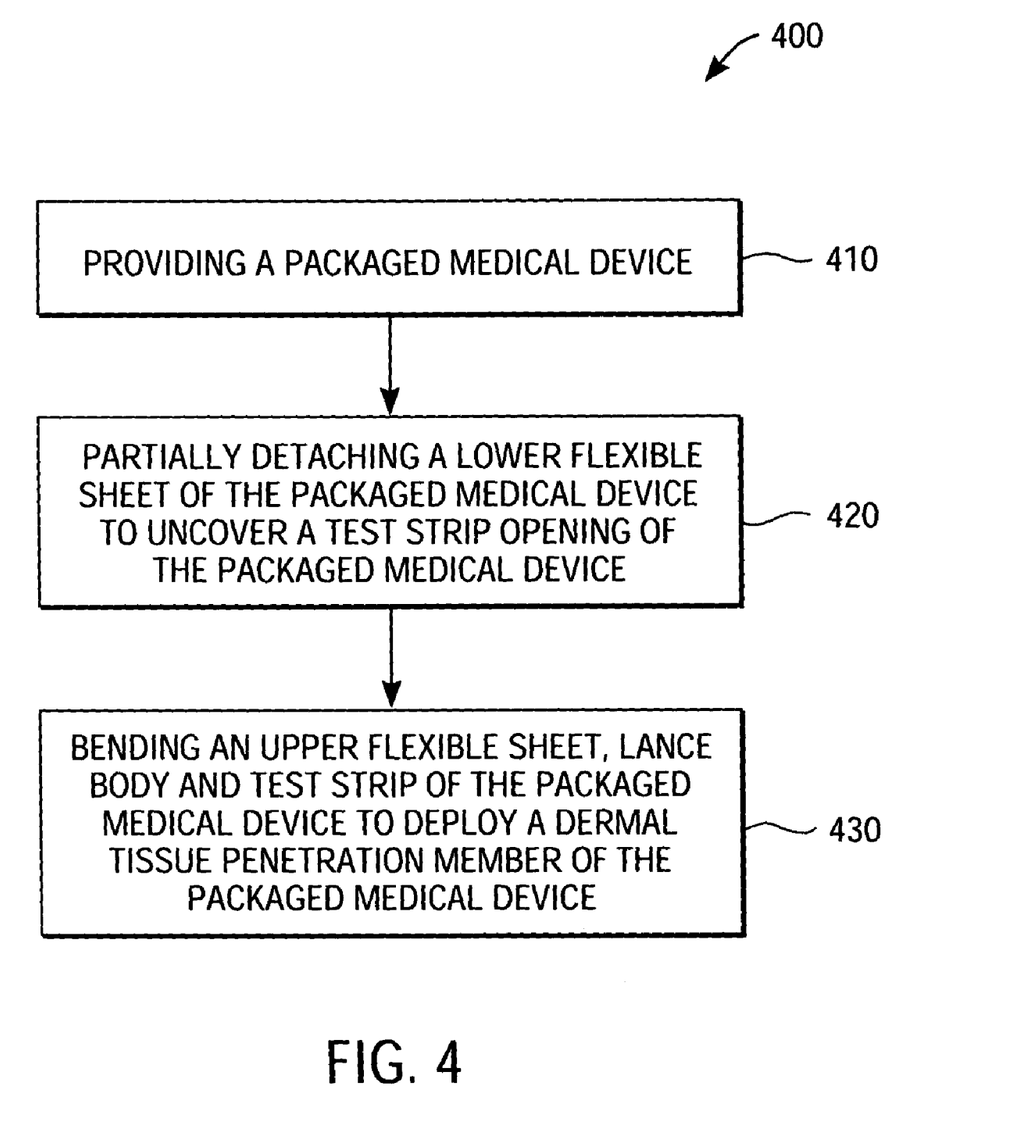
FIG. 4 is a flow chart illustrating a sequence of steps in a process for deploying a dermal tissue penetration member of a packaged medical device according to an exemplary embodiment of the present invention.
Figures 5A, 5B:
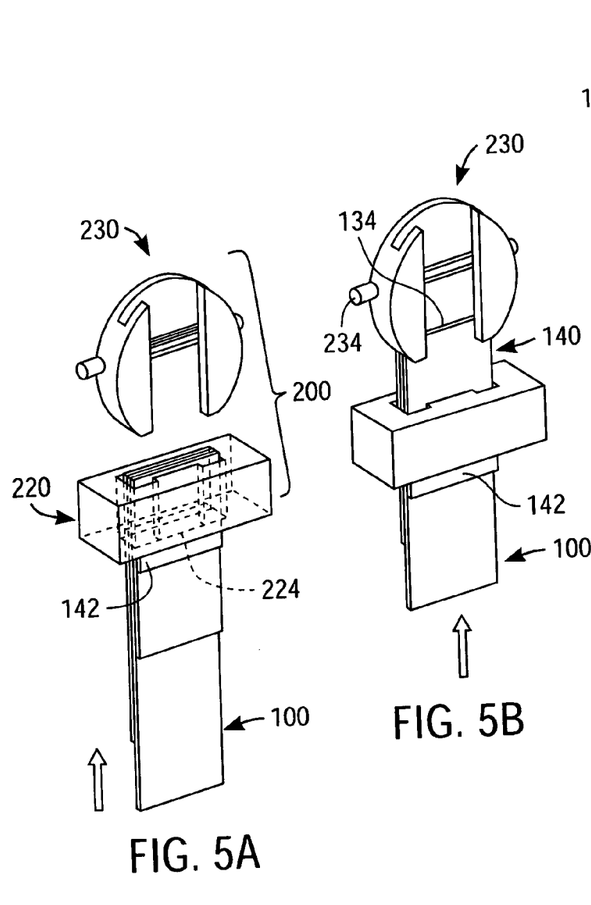
FIGS. 5A–D are schematic, perspective views depicting steps used to deploy a dermal tissue penetration member (e.g., a lancet) of a packaged medical device.

Process 400 includes first providing a packaged medical device 100 as described above with respect to FIG. 1, as set forth in step 410 of FIG. 4. Alternatively, both a packaged medical device and a deployment device (such as the kit of FIG. 2) can be provided, as depicted in FIG. 5A.

Figure 5C:
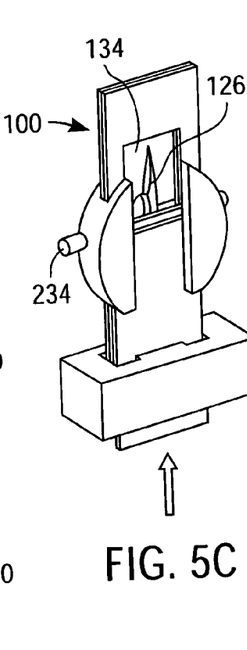

Next, the lower flexible sheet of the packaged medical device is at least partially detached from the test strip of the packaged medical device to uncover the test strip opening, as set forth in step 420 of FIG. 4. This detaching step can be accomplished manually by a user or by use of the deployment device described with respect to FIG. 2 above. In this regard, FIGS. 5B and 5C depict the use of deployment deice 200 to detach the lower flexible sheet. In FIGS. 5B and 5C, an arrow indicates the insertion direction of packaged medical device 100 into deployment device 200.

Figure 5D:
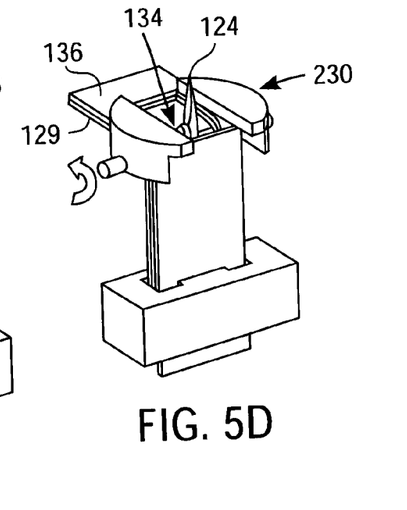

Subsequently, at step 430 of FIG. 4, the upper flexible sheet, lance body and test strip of the packaged medical device are bent (e.g., bent manually or by use of the deployment device described above) to deploy the dermal tissue penetration member from the lance body opening. Such bending is illustrated in FIG. 5D for the circumstance that the deployment device of FIG. 2 is employed. In FIG. 5D, the curved arrow indicates the direction of bending.

If desired subsequent to deployment and use, the upper flexible sheet, lance body and test strip of the packaged medical device can be bent back to their essentially original positions such that the dermal issue penetration member is again projecting into the lance body opening. This can be accomplished either manually or, in the circumstance that a deployment device was employed for bending, by employing the axis pin of the deployment device to return the upper flexible sheet, lance body and test strip of the packaged medical device back to their essentially original positions. In other words, the axis pin would be employed to pivot the folding block in reverse through the arc that had bent the upper flexible sheet, lance body and test strip.

Once the upper flexible sheet, lance body and test strip have been bent back to their essentially original position, the lower flexible sheet can, if desired, be reattached to the test strip to recover the test strip opening. Such reattachment is facilitated if, for example, a resealable adhesive was to detachably attach the lower flexible sheet to the test strip. Once the dermal tissue penetration member is again projecting into the lance body opening and the lower flexible sheet is reattached, a user is protected from inadvertent contact with the dermal tissue penetration member.

One skilled in the art will recognize that the processes according to the present invention can be conducted within a combined sample collection and metering system designed for in-situ testing. Examples of systems designed for in-situ testing are disclosed in International Patent Application No. PCT/US01/07169 (published as WO 01/64105 A1 on Sep. 7, 2001) and International Patent Application No. PCT/GB02/03772 (published as WO 03/015627 A1 on Feb. 27, 2003), each of which is fully incorporated herein by reference. In addition, the mechanical motions required for deploying a dermal tissue penetration member can be combined with lancet cocking and/or strip loading. Alternatively, motorized components may separately perform the stripping and folding actions.

While preferred embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A packaged medical device comprising:
    an upper flexible sheet;
    a lance body that includes:
        a lance body upper surface;
        a lance body lower surface;
        a lance body opening extending from the lance body upper surface to the lance body lower surface; and
        a dermal tissue penetration member projecting into the lance body opening;
    a test strip with a test strip opening therethrough; and
    a lower flexible sheet,
wherein:
    the upper flexible sheet is attached to the lance body upper surface covering the lance body opening;

the test strip is attached to the lance body lower surface such that the dermal tissue penetration member is operatively aligned with the test strip opening;

the lower flexible sheet is detachably attached to the test strip covering the test strip opening; and the upper flexible sheet, lance body and test strip are configured such that, when the lower flexible sheet has been at least partially detached from the test strip, thereby uncovering the test strip opening, the upper flexible sheet, lance body and test strip can be bent such that a bent portion of the upper flexible sheet, lance body, and test strip moves away from the packaged medical device as the packaged medical device remains essentially stationary, thereby deploying the dermal tissue penetration member from the lance body opening.

2. The packaged medical device of claim 1, wherein the test strip is an electrochemical test strip.

3. The packaged medical device of claim 1, wherein the test strip is a colorimetric test strip.

4. The packaged medical device of claim 1, wherein the test strip is a glucose measurement test strip.

5. The packaged medical device of claim 1, wherein the upper flexible sheet, lance body and test strip can be bent through an arc in the range of approximately 90 degrees to approximately 100 degrees to deploy the dermal tissue penetration member.

6. The packaged medical device of claim 1, wherein the packaged medical device is formed using lamination techniques.

7. The packaged medical device of claim 1, wherein the test strip includes at least one electrode contact and the upper flexible sheet is attached to the lance body upper surface and the test strip is attached to the lance body lower surface such that the at least one electrode contact extends beyond the lance body and the upper flexible sheet.

8. A kit comprising:
a packaged medical device that includes:
an upper flexible sheet;
a lance body that includes:
a lance body upper surface;
a lance body lower surface;
a lance body opening extending from the lance body upper surface to the lance body lower surface; and
a dermal tissue penetration member projecting into the lance body opening;
a test strip with a test strip opening therethrough; and
a lower flexible sheet,
wherein:
the upper flexible sheet is attached to the lance body upper surface covering the lance body opening;
the test strip is attached to the lance body lower surface such that the dermal tissue penetration member is operatively aligned with the test strip opening;
the lower flexible sheet is detachable attached to the test strip covering the test strip opening; and
the upper flexible sheet, lance body, and test strip are configured such that, when the lower flexible sheet has been at least partially detached from the test strip, thereby uncovering the test strip opening, the upper flexible sheet, lance body and test strip-can be bent to deploy the dermal tissue penetration member from the lance body opening; and
a deploying device configured for at least partially detaching the lower flexible sheet from the test strip and bending of the upper flexible sheet, lance body and test strip such that a bent portion of the upper flexible sheet, lance body and test strip moves away from the packaged medical device as the packaged medical device remains essentially stationary, thereby deploying the dermal tissue penetration member from the lance body opening.

9. The kit of claim 8, wherein the deploying device includes:
a stripping block for at least partially detaching the lower flexible sheet from the test strip; and
a folding block for bending the upper flexible sheet, lance body and test strip to deploy the dermal tissue penetration member.

10. The kit of claim 8, wherein the test strip is an electrochemical test strip.

11. The kit of claim 8, wherein the test strip is a colorimetric test strip.

12. The kit if claim 8, wherein the test strip is a glucose measurement test strip.

13. The kit of claim 8, wherein the packaged medical device is a laminated packaged medical device.

* * * * *